United States Patent [19]
Beevor

[11] Patent Number: 6,122,344
[45] Date of Patent: Sep. 19, 2000

[54] X-RAY INSPECTION SYSTEM

[75] Inventor: Simon P. Beevor, Farnborough, United Kingdom

[73] Assignee: The Secretary of State for Defence in Her Brittanic Majesty's Government of the United Kingdom of Great Britain and Northern Ireland, Farnborough, United Kingdom

[21] Appl. No.: 08/875,903

[22] PCT Filed: Jan. 30, 1996

[86] PCT No.: PCT/GB96/00195

§ 371 Date: Oct. 20, 1997

§ 102(e) Date: Oct. 20, 1997

[87] PCT Pub. No.: WO96/24863

PCT Pub. Date: Aug. 15, 1996

[30] Foreign Application Priority Data

Feb. 8, 1995 [GB] United Kingdom .................. 9502460

[51] Int. Cl.[7] .................................................. G01N 23/201
[52] U.S. Cl. ................................................ 378/88; 378/57
[58] Field of Search ........................................ 378/88, 57

[56] References Cited

U.S. PATENT DOCUMENTS

| 4,956,856 | 9/1990 | Harding ..................................... 378/88 |
| 5,007,072 | 4/1991 | Jenkins et al. ............................ 378/88 |
| 5,231,652 | 7/1993 | Harding . |
| 5,428,657 | 6/1995 | Pananicolopoulos et al. ........... 378/88 |

FOREIGN PATENT DOCUMENTS

| 0 311 177 | 4/1989 | European Pat. Off. . |
| 0 354 045 | 2/1990 | European Pat. Off. . |
| 0 358 965 | 3/1990 | European Pat. Off. . |

Primary Examiner—Craig E. Church
Attorney, Agent, or Firm—Nixon & Vanderhye P.C.

[57] ABSTRACT

An X-ray inspection system comprises an X-ray source (1) disposed to irradiate an object to be inspected (4) with a beam of X-rays in the form of a fan project from the source (1) through the object (4), detection means (6) capable of discriminating between the intensitities of X-rays coherently scattered through the object (4) at different angles to produce an output signal dependent on the intensity of the X-rays scattered through each of those angles and analyzing means (not shown) operably connected to the detention means (6) to process the output signal to determine the presence of X-rays coherently scattered through one or more predetermined angles. Collimination means (23) is provided between the detection means (6) and the object (4) and is adapted to pass only X-rays coherently scattered at the different angles from a limited voxel (volume element) depth central at point P. Movement at the collimator (23) along the direction of the beam together with translation of the object by e.g. a conveyor (5) in the direction (22) allows the whole volume of the object, such as an item of baggage, to be scanned.

20 Claims, 6 Drawing Sheets

Increasing angle of scatter →

Fig.5(B).

Scattering intensity

Increasing angle of scatter →

X-RAY INSPECTION SYSTEM

BACKGROUND OF THE INVENTION

1. Field of the Invention

This invention relates to the field of X-ray inspection systems and more particularly those inspection systems which use coherently scattered X-rays to detect the presence of explosives, incendiary materials, prohibited drugs or other illegally transported substances (hereinafter collectively referred to as "target material") in a container, the presence of imperfections or impurities in a material or object or the non-destructive, spatially-resolved, chemical analysis of an object.

2. Discussion of Prior Art

As the problems discussed in relation to known inspection systems below are equally valid for container, object and material inspection systems they will be discussed only in relation to container inspection systems. The term "container" shall hereinafter be taken to refer to both the container and its contents.

Many systems which utilise X-rays have been developed for the inspection of containers such as baggage and parcels. These include dual energy transmission imagers, backscatter imagers and computer-aided tomography (CAT) scanners all of which essentially yield effective atomic number and density information in two or three dimensions. However, these systems are inherently chemically non-specific and rely heavily on operator vigilance and interpretation during visual inspection of the spatial distribution of the contents of the containers and on other indicators such as the presence of initiating devices in the case of explosive target materials. A problem here is that many kinds of target material are not easily identifiable by their shape since they can be easily moulded or packed inside other items within the container to mask their presence. Furthermore, initiating devices are often masked by adjacent clutter within the container. These materials, and more specifically explosive devices, are therefore not readily detectable using these systems.

One known system which overcomes this problem is described in the U.S. Pat. No. 4,751,722 (EP 0,153,786). This discloses a system which analyses the intensities of X-rays which are coherently scattered through different small angles when passing through a container. This information is then used to generate an angle dispersive X-ray spectrum which is characteristic of the ordered molecular structure of the material responsible for the scattering. The X-ray spectrum may then be passed to a data processing system where an automatic comparison is made with stored spectra characteristic of the target materials of interest in order to determine whether or not these target materials are present within the container.

However a problem with this system is that the contents of a container can only be resolved in the two dimensions of the scattering voxel (volume element) in the plane perpendicular to the direction of travel of the unscattered X-rays, ignoring the third dimension in the direction of the unscattered beam, through the depth of the container. Where either the container or the target material has a third dimension greater than a few centimeters then depth resolution is required in order to satisfactorily identify the presence of a target material. This is because coherent scattering over a range of scattering angles from non-target materials at different depths within a container cannot be differentiated from the scattering caused by localised target material at any given angle of interest thereby causing the generated X-ray spectrum to become confused and identification of target material difficult.

A further problem with this earlier system is that the low X-ray flux generated by presently available monochromatic sources results in too great an inspection time, making it impractical to use in situations where a large number of objects of large size need to be rapidly inspected eg. such as for containers in airports. However, the use of a high intensity polychromatic source would degrade the material discrimination capability of the system.

UK patent No. 1,463,054 provides a means of examining a body, eg. a human skull, in which the body is mapped in two dimensions including the vertical dimension, for the purpose of determining the position of scatter centres within the body. Whilst this equipment is capable of scanning through the depth of the body being examined its use of conical collimators or annular detectors limits the flexibility of the system in a manner which is significantly disadvantageous for the purposes of materials detection as it is not possible to arrange for simultaneous inspection of more than one closely spaced voxel using a single X-ray source. The method is inherently incapable of providing the chemically specific information which is required of a detection system of the type with which the present invention is concerned.

Another known X-ray detection system is shown in FIGS. 1 to 4 of U.S. Pat. No. 4,956,856. This uses long thin X-ray detectors, which must be longer than the body to be examined, to measure scattering spectra from small volumes within an object in three dimensions. This patents concedes that for the inspection of baggage such long detectors would have insufficient spatial resolution for the accurate determination of scattering spectra. This would lead to poor material discrimination. Similar results would be obtained using these detectors for the inspection of any object of moderate diameter, even for those objects with diameters significantly less than typical luggage. Furthermore, such an equipment could not operate with good material discrimination using a polychromatic X-ray source, such as an X-ray tube, as the energy resolution of the scintillator based X-ray detectors which are used is insufficient. A monochromatic source would be required for good discrimination with similar implications for inspection times as noted for U.S. Pat. 4,751,722 above.

The embodiment depicted in FIGS. 5 to 7 of U.S. Pat. 4,956,856 uses a gamma (or Anger) camera based X-ray detector which cannot be implemented with sufficient photon energy resolution for good material discrimination as this detector is similarly scintillator based. In this invention it is also necessary to displace the object under inspection (or alternatively the source, collimator system and detector) along two perpendicular axes, or the object along one axis and the source, collimation system and detector along another perpendicular axis, in order to carry out full three dimensional inspection of the object. This is mechanically complex and time consuming. A further difficulty is that the number of regions of the path of the unscattered X-ray beam through the object which can be independently inspected will be limited by the diameter and spatial resolution of the gamma camera.

U.S. Pat. No. 5,007,072 (EP 0,354,045) describes another X-ray inspection system, again inspecting an object in only two dimensions with the drawbacks outlined above for U.S. Pat. No. 4,751,722 and further detecting only at a set angle and measuring the wavelength spectrum of radiation scattered at that angle. To do this also requires the use of expensive and complex solid state germanium or silicon detector arrays operating at cryogenic temperatures. Likewise the detector disclosed in U.S. Pat. No. 5,265,144 is based on measurement of the energy of scattered radiation at a fixed scattering angle. Moreover in the case of this detector it is focussed on a small area within the object being examined and is only able to inspect voxels arranged in one dimension through the object by translation of the relative positions of the detector and collimator systems and the object. Full three-dimensional inspection with this system would require translation of the object or of the source, detector and collimator systems in a total of two further perpendicular dimensions. This would not provide a practicable equipment in the context of a baggage inspection system.

Finally, a further patent, U.S. Pat. No. 4,754,469, discloses a detection equipment which employs a monochromatic X-ray source, with consequent long inspection periods, or expensive and complex solid state cryogenically cooled germanium or silicon detector semiconductor arrays for good material discrimination. Translation of the object under inspection or of the X-ray source, collimation system and detector arrays together in a combined total of two mutually perpendicular axes is also required for two dimensional analysis. Three dimensional inspection would only be achievable by additionally displacing the relative positions of the object or of the truncated detector collimator.

SUMMARY OF THE INVENTION

It is an aim of the present invention to provide an X-ray inspection system which alleviates at least some of the aforementioned problems.

It is well known that in crystalline materials incident X-rays can be coherently scattered from the crystal lattice. The angle, $2\theta$, measured relative to an axis through the source and scattering centre, at which the X-rays are coherently scattered is dependent on the wavelength, $\lambda$, of the incident X-rays and on the crystal lattice spacing, d, and satisfies the equation:

$$n\lambda = 2d \sin \theta \quad (1)$$

where n is a positive integer. Thus by detecting the presence of incident X-rays of a known wavelength, $\lambda$ (or a multiple thereof), which have been coherently scattered through known angles, $2\theta$, satisfying equation (1) above, the crystalline target material responsible for the scattering can be identified.

However, it is also known from published work, such as that of Harding and Kosanetzky (J Opt Soc Am A, Vol. 4, No. 5, p 933–944, May 1987), that this technique is not limited to the discrimination and analysis of purely crystalline materials but can also be applied to non-crystalline or poorly ordered materials such as polymers and organic materials. Similarly the wide range of explosives which are mixtures of a crystalline, usually energetic explosive components, and non-crystalline, usually non-explosive materials, can be identified.

According to the present invention there is provided an X-ray inspection system comprising a collimated X-ray source disposed to irradiate an object to be inspected with a beam of X-rays projected from the source through the object, said beam of X-rays being in the form of a fan in a plane perpendicular to the plane of scattering of the X-rays; detection means capable of discriminating between the intensities of X-rays coherently scattered through the object at different angles to produce an output signal dependent on the intensity of the X-rays scattered through each of those angles; collimation means disposed between the detection means and the object and which is adapted to pass only X-rays coherently scattered at the different angles from a limited voxel depth and from a limited arc of the fan beam; and analysing means operably connected to the detection means to process the output signal to determine the presence of X-rays coherently scattered through one or more predetermined angles, wherein the and wherein the collimation and detection means are adapted to detect X-rays across the width or spread of the fan beam.

The term "fan beam" as used herein should be understood as including beams which are in the form of either a continuous fan or a discontinuous fan, that is to say in the latter case, an otherwise continuous fan in which one or more small arcs are fully attenuated. Such a discontinuous beam is referred to herein as a "broken fan beam".

The collimation means provides depth resolution in the direction of the X-ray beam which has the advantage that since only a limited depth of the object is inspected at any time then discrimination between scattering from the target and that from other material is enhanced, as is discrimination between scattering at different angles from different depths of target material.

Usefully either or both of the collimation means and the object may be made moveable relative to one another in the direction of the (unscattered) X-ray beam so as to vary the position of the voxel through the depth of the object. In this way substantially the entire depth of the object can be inspected. For ease of construction it is preferable if only the collimation means so moves. However, where the collimation means is moveable, it may be more advantageous to provide a detection means capable of moving conjointly with the collimation means so as to maintain the relative separation between the two. This has the advantage that scattering through any given angle will be detected at substantially the same position on the detection means irrespective of the position of the voxel through the depth of the object.

The collimation means may comprise a plurality of sheets of X-ray attenuating material each extending along different radii of circles having centres coincident with the centre of a given two dimensional voxel, with both each circle and the corresponding voxel being in a plane perpendicular to the plane of the fan beam from which scatter may be detected. Conveniently each sheet is spaced apart from adjacent sheets by a small angle, subtended at the centre of the aforementioned circle, of typically 0.5 degrees. The centres of a number of parallel, closely spaced two dimensional scattering voxels across a limited arc of the fan beam are preferably collinear along a line perpendicular to a plane which is in turn perpendicular to the plane of the fan beam. If this small angular separation remains constant then the collimation means provides a small scattering voxel depth, in the direction of the unscattered X-ray beam, which depth is dependent on scattering angle.

Instead of the sheet spacing being constant as described, in a second embodiment of the collimator where it is desired to arrange for a constant voxel depth irrespective of the scattering angle, $2\theta$, then the radial separation, s, of the sheets should be calculated according to the equation:

$$s = (C \times \tan(2\theta)) + w \quad (2)$$

where C is a constant dependent on both the required voxel depth and on instrumental dimensions and w is dependent on the instrumental dimensions and the sheet width.

In the previously described collimator embodiments with constant or variable sheet spacing, periodic total attenuation of the scattered X-ray beam with angle is experienced if a scattering pattern is acquired using a stationary collimator. Total attenuation at discrete scattering angles can be avoided for these embodiments by rotating the collimation means during the course of scattering profile acquisition, by a small angle (typically equal to the angular spacing of the sheets), about the centre of the corresponding two dimensional scattering voxel in a plane perpendicular to the fan beam but coplanar with the two dimensional scattering voxel. The period of rotational movement may be small compared to the period of the scattering profile acquisition or be essentially of the same duration.

A preferred third embodiment of collimator however avoids total attenuation of the scattered X-ray beam at any scattering angle without the requirement for rotational motion of the collimator. This third embodiment is conceptually identical to the first two embodiments and may be employed as above with collimator sheets placed at constant angular spacings or a range of angular spacings, as required. However in this embodiment, over a small arc of the fan beam which is centered on the middle of the beam, the sheets, instead of being placed along the planes of radii from the centrally collinear parallel two dimensional scattering voxel centres as described above, are rotated from this position by an angle which, for sheets which have constant spacing, is typically in the range of from 5 to 25, more especially around 15 degrees, about an axis extending from the centre of the two dimensional scattering voxel to the mid point of the said small arc. Thus the attenuation of the scattered X-ray beam can preferably, with a suitable choice of the angle of rotation of each individual sheet, be made small and closely equivalent at all scattering angles when the summed signal passing through the collimator from all of the constituent centrally collinear, parallel two-dimensional scattering voxels within the small arc across the fan beam concerned is accumulated.

Advantageously the angle of rotation of each sheet about an axis from the centre of the two dimensional scattering voxel which is coplanar to the central radius of the small arc across the fan beam concerned to the mid point of the same small arc may vary with distance from the scattering voxel centre along this axis. Most preferably the angle of rotation will be linearly proportional to the distance from the scattering voxel centre.

In a preferred embodiment the X-ray source comprises a polychromatic X-ray generator and a co-operable balanced filter system. This has the advantage that the inspection time for a object may be reduced as compared with the inspection time required when the X-ray source consists of a monochromatic X-ray generator. The polychromatic generator provides a relatively high beam flux which allows for the rapid inspection of objects while the balanced filter system, used according to the method of Cooper et al (J. Phys E, 1985, Vol 18, p 354) provides an effective band-pass X-ray photon energy filter and permits the generation of an apparent angle dispersive X-ray spectrum substantially equivalent to one which would have been generated had a substantially monochromatic X-ray source been used. Furthermore, by arranging for each filter to be automatically placed in the beam path the need for operator intervention is removed.

A detector with moderate X-ray photon energy discrimination being sensitive to substantially only those X-ray energies close to the band-pass region of the balanced filter system, for example one comprising a position sensitive photomultiplier tube coupled to an X-ray scintillator material, may be usefully employed in conjunction with the polychromatic X-ray generator and balanced filter system to reduce a large proportion of Bremstrahlung radiation produced outside the X-ray photon energy region of interest. By so doing the signal to noise ratio of the generated spectrum is increased, thereby allowing for a further reduction in inspection time.

Advantageously the detection means may be capable of simultaneously detecting X-rays scattered through a range of angles containing those predetermined angles of interest, for example by employing an imaging detector system or a number of discrete detector elements each arranged to detect at different discrete angles or narrow spread of angles, to produce an angle dispersive X-ray spectrum. This has an advantage that the inspection time for each object is reduced since data for the whole range of scattering angles of interest can be collected in parallel.

Preferably the detection means and collimation means are adapted to independently detect X-rays across the fan beam from small arcs of the fan beam, typically less than 1 degree. This serves to further reduce the inspection time for each object and provides resolution of materials along the longest axis of the fan beam.

Most usefully there is also provided a means, such as a conveyor belt, for transporting the object to be inspected through the fan beam.

The conveyor serves to allow translation of the two dimensional inspection slice provided by the motion of the collimator as previously described and the height of the fan beam, collimation and detection means, through the full length of the object. Motion of the object on the conveyor during signal acquisition may also be advantageously used to disperse over a wider angular scattering range the attenuation effects of materials outside the scattering voxel but within the arc of scattered radiation which may otherwise distort the scattering pattern obtained from the contents of the scattering voxel. This is implemented by acquiring a scattering pattern over a period during which the object moves a significant distance on the conveyor through the fan beam. However the displacement of the object during this period should be less than the width of the volume of target material to be examined in the direction of conveyor motion or scattering contributions from regions containing materials other than the target material may dominate the combined scattering pattern and confuse pattern matching with resultant loss of materials discrimination.

Most advantageously the X-ray inspection system may additionally comprise an alarm means operably connected to the analyser means for producing an audio, visual or audio-visual alarm when the presence of X-rays scattered with certain relative intensities at one or more pre-determined angles has been determined. This provides a warning to an operator that a target material or the like has been detected within an object.

In order to increase the signal to noise ratio and hence the reliability of the system it is preferable that the analyser means is further adapted to process a signal formed from a number of voxels to be representative of the total signal from a localised region of the object under inspection to determine the presence within that region of X-rays scattered with certain relative intensities at one or more pre-determined angles.

Given the limited inspection rates predicted for coherent X-ray scatter inspection of large objects such as baggage, the likely expense of such equipment and the capabilities of existing equipments such as dual energy X-ray transmission and CAT X-ray inspection equipments, an adaptation of the above invention is suggested in which inspection is limited to a fraction of the full volume of the object following direction of the inspection by a preliminary, less discriminating but faster technique such as those prior art methods mentioned previously, to examine a localised volume considered likely to contain the threat material, in the case of aircraft baggage, or worthy of further analysis in more general terms. In the case of aircraft baggage such a second level coherent scatter equipment would complement the density, average atomic number and spatial information obtained from conventional first level equipments by supplying a fourth independent piece of information describing the crystallographic or chemical structure of the target material. However, this would only be employed when the threat from a material in a given volume of the bag remained unresolved after analysis using first level information.

Such a directed coherent X-ray scatter equipment could be implemented using the invention described herein and would require a fraction of the instrumentation required for full baggage inspection. For example, a limited fan beam of X-rays, covering a height of, say, 10 cm, could be used with ⅙th of the collimation and detection systems required to inspect a typical full sized suitcase, 60 cm in height by 90 cm long, to interrogate through the full depth of the case over a 10×10 cm area in ⅙th of the inspection period for the full case.

The X-ray system of this invention is preferred for baggage and many other scenarios of container inspection to an X-ray inspection system in which full annular detection of scattered photons from a single voxel is used. In the latter configuration of equipment it is not practicable to arrange detector arrays to allow less than full manipulation of the baggage and/or the collimation systems in three dimensions. Furthermore it is not advantageous to accept the mechanical complexity of three-dimensional manipulation as the signal count rate from a single voxel will remain comparable in an annular detection based three-dimensional system to the two-dimensional manipulation and fan beam arrangement described herein. This is because in general to maintain spectra resolution the primary photon beam width must be kept small, typically 1 mm, along the axis of spectral measurement. In this invention this is accomplished but it is also possible to increase the primary beam height over which scatter is recorded from a single voxel and the height of the detection area from which scatter is recorded from a single voxel to greater than this distance, typically around 10 mm, without significantly degrading spectral resolution in order to obtain a larger signal.

In an annular detection based X-ray inspection system the height of the primary beam from which scatter is recorded from a single voxel must remain equivalent to the width (i.e. a circular primary beam cross section should in principle be used) or the spectral resolution along the height axis will be degraded and this contribution will degrade the resolution of the total scatter pattern. The same considerations apply with respect to the maximum dimensions of the X-ray tube focal spot which can be used without degrading spectral resolution. In the case of an annular detection based X-ray system, and in a similar manner to the beam width, the focal spot should be circular with a diameter that does not significantly degrade spectral resolution along any signal measurement axis. The same restriction applies along the axis of measurement in this invention but not along the perpendicular axis where the spot may be much larger thus giving a higher signal count rate with negligible loss of spectral resolution. In this invention an X-ray tube focal spot is typically 1×3 mm.

More advantageously a full three dimensional mapping of the attenuation of an object at the X-ray photon energies concerned, in other words tomographic information, could be used to correct for the attenuation effects of materials both in the unscattered primary beam and the arc of scattered photons. In the case of monochromatic X-ray diffraction using balanced filters the attenuation information should be obtained in the small X-ray energy band-pass range concerned, i.e. 57.49 to 59.38 keV. Such information can be obtained using known tomographic methods such as that described in U.S. Pat. No. 4,730,350.

BRIEF DESCRIPTION OF THE DRAWINGS

Embodiments of the X-ray inspection system according to the present invention, when employed to inspect containers, will now be described with reference to the accompanying drawings in which:

FIG. 5 shows (A) a typical scattering image and (B) a reduced information scattering profile produced from this image;

DETAILED DISCUSSION OF PREFERRED EMBODIMENTS

Figure 1:
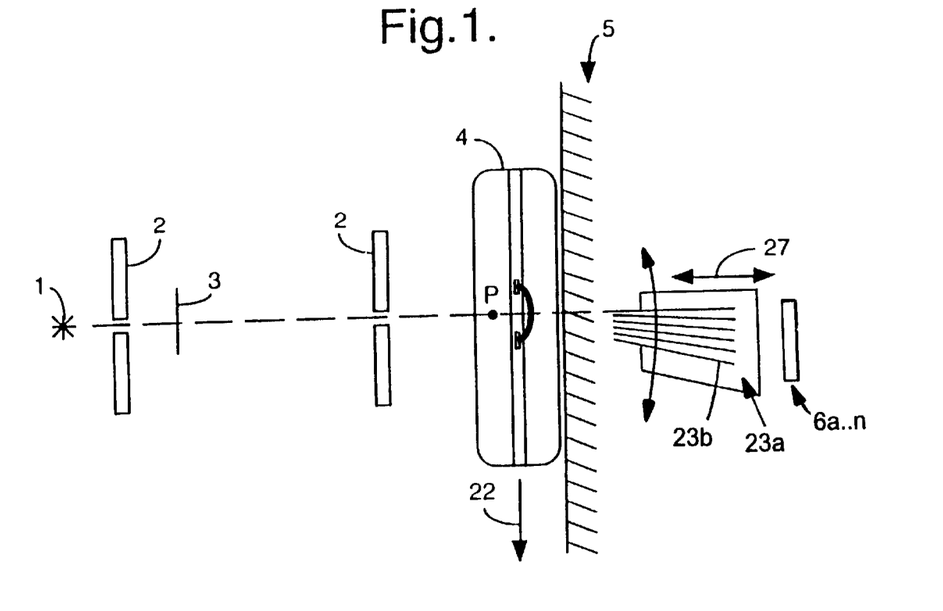
FIG. 1 is a partial cross section viewed from overhead of an X-ray inspection system.
Figure 2A:
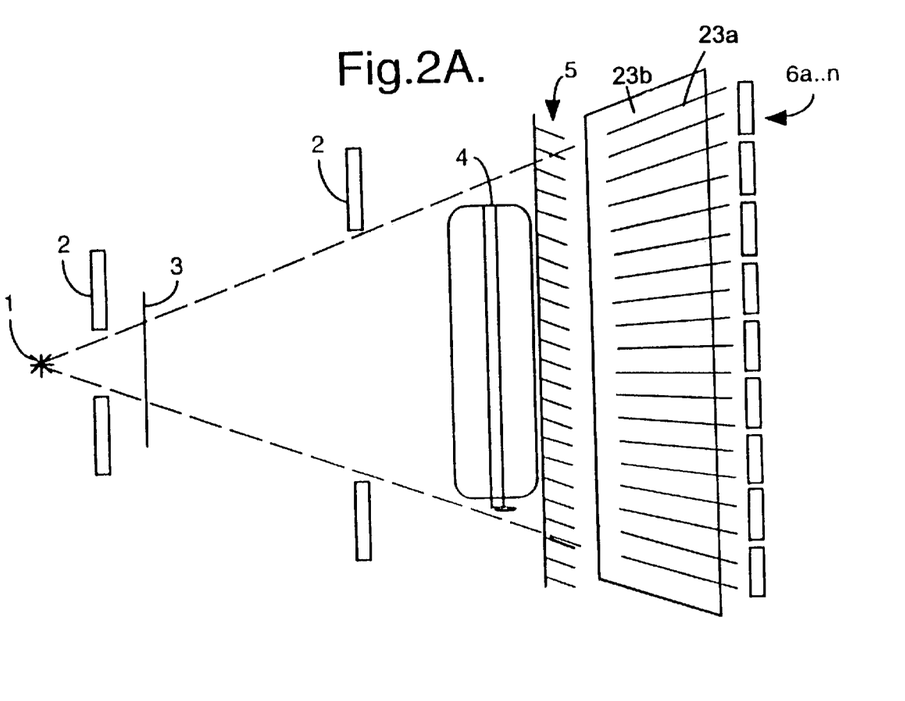
FIG. 2A is a side view of the same system showing the fan beam.

Referring now to FIGS. 1 and 2A which are mutually perpendicular views of the same embodiment of the invention, X-rays from the polychromatic X-ray source 1 are collimated into a narrow continuous or broken fan beam by the slit collimators 2. This fan beam (seen more clearly in FIG. 2A) passes through a filter in the balanced filter system 3 before being incident upon a container 4 which is on a conveyor belt 5 moving at a constant velocity in the direction of 22. The balanced filter system 3 has two filters which when used sequentially act as a single, narrow photon energy range, band-pass filter. The first filter is constructed from thulium and the second filter from erbium which together advantageously have K absorption edges which bracket the tungsten $K\alpha 1$ and $K\alpha 2$ fluorescence lines of a tungsten anode X-ray source.

X-rays passing through this container 4 and which are elastically scattered through a range of angles $2\theta$ by target material within the container 4, are collimated in the plane of FIG. 1 by an array of metal foil sheets 23b (typically 0.3 mm steel sheet) arranged normal to the plane of the Figure and along radii of a circle centred at point P within the container 4 such that scatter from only a limited voxel depth (typically 2–3 cm) centred at P, for the range of angles of interest (typically 1 to 10 degrees), is capable of being detected.

The radial separation of adjacent sheets may be calculated using equation (2) for which a value of C=2.08 is obtained for a constant voxel depth of 2 cm; a distance between the point P and the nearest edges of the sheets of 25 cm, a sheet length of 25 cm and a value for w of 0.12 for a sheet width of 0.3 mm at these dimensions.

In order to inspect the full depth of the container 4, the sheets 23b are moveable together (as indicated by arrow 27) along the direction of the unscattered X-ray beam (as represented by the broken line in FIG. 1) so as to move the inspection centre P by the same amount as the sheets 23b are moved.

Referring to FIG. 2A, the collimated X-rays are detected simultaneously over all of the range of angles, 2θ, by one of an array of detectors 6a . . . n which are disposed across the width of the fan beam. Each of the detectors 6a . . . n comprises a large format photon counting camera, for example an X-ray image intensifier tube and low noise camera combination or a scintillator and intensified CCD camera, having a spatial resolution of the order of hundreds of microns and a sensitive area of several square centimeters or more over which incident X-rays can be detected. The individual detectors 6a . . . n are arranged to produce an output representative of the intensities and positions of scattered X-rays incident upon the detector. Each detector is also collimated in a plane perpendicular to the fan beam by sheets 23a as shown in FIG. 2A, such that each detector records scatter only from a limited arc of the fan beam.

Figure 2B:
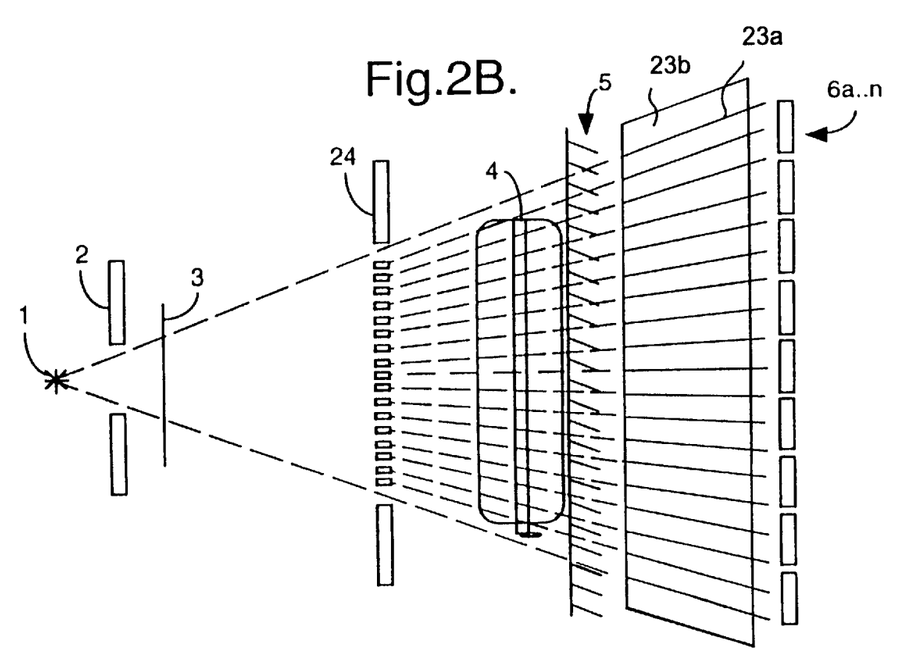
FIG. 2B is a side view of the same system but in which the X-ray beam is a broken fan beam.

FIG. 2B is the same basic arrangement as in FIGS. 1 and 2A except that the second of the two primary beam collimators 2 of the former arrangement is replaced by a collimator plate 24 in which the single continuous slot used before to produce a continuous fan beam is divided into a series of short slots. Consequently a discontinuous (or "broken") primary fan beam is produced. Such a beam will have a collimating effect which may be used in addition to or independently of the collimating effect achieved in the plane perpendicular to that of the fan beam such that each detector records scatter only from a limited arc of the fan beam, as previously described.

Figure 3:
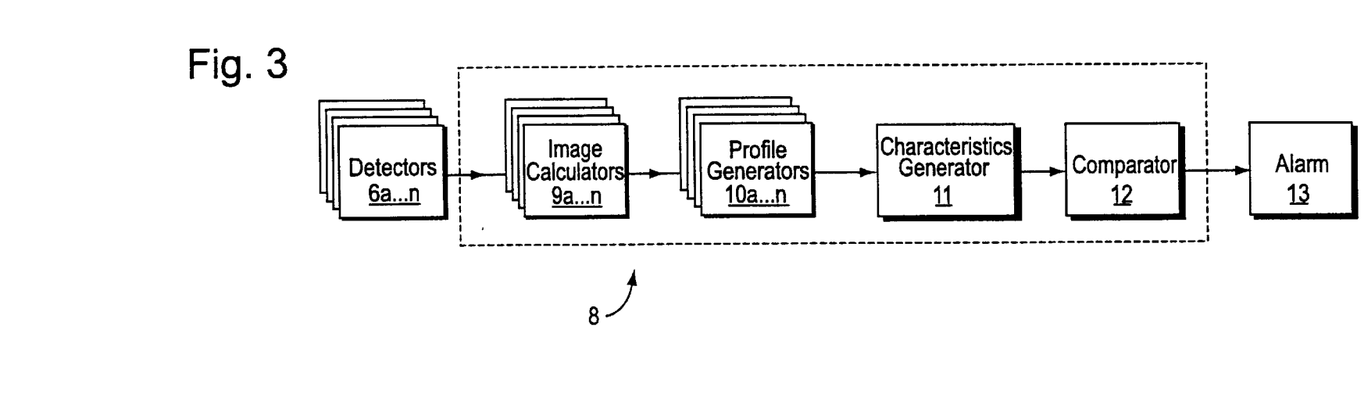
FIG. 3 is a schematic representation of a first embodiment of the analyser means.

Referring now to FIG. 3, the output signal from each of the detectors 6a . . . n is then passed to the analysing means 8, depicted by the broken lines, which comprises an array of differential image calculators 9a . . . n, one for each detector 6a . . . n; an array of scattering profile generators 10a . . . n, one for each calculator 9a . . . n; a spectrum characteristics generator 11 and a spectrum characteristics comparator 12.

The output signals from each detector 6a . . . n are acquired into an associated differential image calculator 9a . . . n to produce a scattering image. Each image is then processed by an associated scattering profile generator 10a . . . n to reduce the amount of data which is passed to the spectrum characteristics generator 11 by discarding information in those parts of the image associated with areas of the detector corresponding to scattering locations through which X-rays are not expected, by equation (1), to be coherently scattered by a target material of interest. The information in those remaining areas representative of a particular scattering angle is then averaged to further reduce the data to be passed to the spectrum characteristics generator 11. This reduced information scattering profile is then passed to the spectrum characteristics generator 11 where the angular positions and intensities of relevant scattering features within the profile are determined. The characteristics measured in each profile are then passed to the spectrum characteristics comparator 12 where a determination is made as to the presence within the container 4 of any target material by comparing these characteristics with those stored in the comparator 12. If it is determined that target material is present an activating signal is sent from the comparator 12 to the alarm 13 which serves to alert the operator to its presence.

Figure 4:
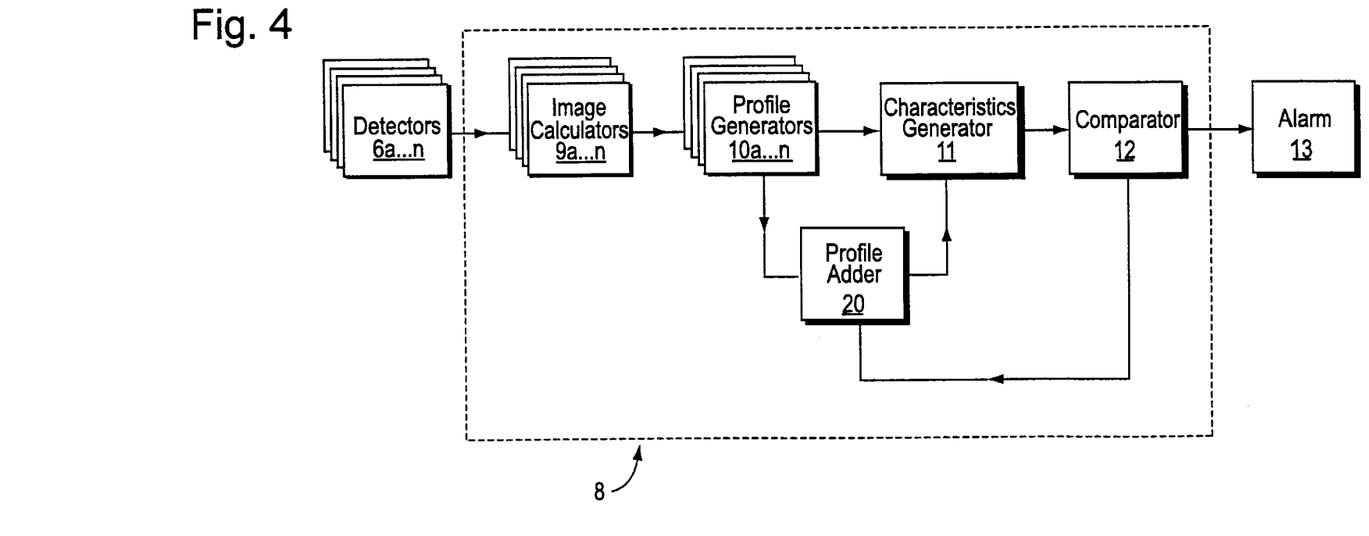
FIG. 4 is a schematic representation of a second embodiment of the analyser means.

In a further embodiment of the invention, shown in FIG. 4, the analysing means 8 is similar to that described above except that a profile adder 20 is incorporated between the profile generators 10a . . . n and the spectrum characteristics generator 11. Either routinely or when the presence of target material has been determined from a single profile, as described above, a first activating signal from the comparator 12 is relayed to the adder 20 which then operates to sum the profiles from a small number of profile generators 10a . . . n to produce a single profile which is representative of X-rays elastically scattered from a localised region of the container. This single profile is then passed to the spectrum characteristics generator 11 and processed as previously described. In the event that the comparator 12 determines the presence of target material from this summed profile a second activating signal from the comparator 12 is relayed to the alarm 13. This affords some protection against an incorrect determination of the presence of target material in one profile because the signal to noise ratio is greater for this profile than for the individual component profiles. Alternatively a coincidence approach may be adopted in which an alarm is only triggered when one or more adjacent volumes are determined to be filled with a given target material.

It will be readily apparent to those skilled in the art that the functions of all of the above described components of the analysing means can be performed by one suitably programmed computer.

During the acquisition of the scattered beam from a particular voxel all of the sheets 23b may be rotated out of the plane of the fan beam about P by a small angle which is typically the smallest spacing of the sheets 23b. This displaces, over time, the radial position of the sheets and avoids loss of information due to total attenuation of the scattered X-rays at the discrete scattering angles in which the sheets are orientated when stationary. The sheets may be returned to their original positions and the same displacement repeated for each voxel which is inspected or the sheets may be displaced alternately by the same amount in opposite directions for alternate voxels.

Figure 7:
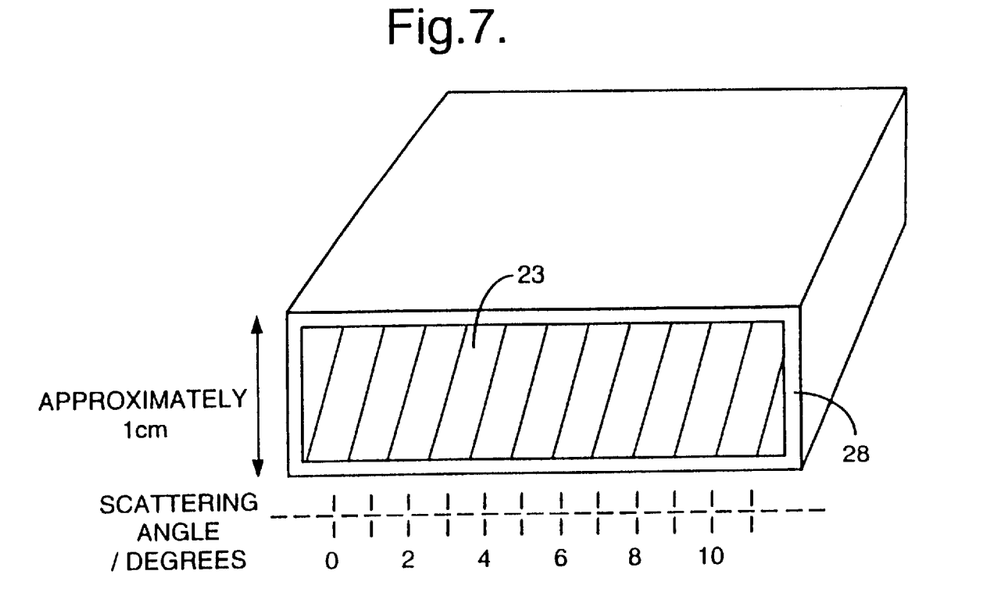
FIG. 7 is a schematic representation of a different embodiment of the collimator to that shown previously, viewed from the direction of the source and being arranged to lie perpendicular to the plane of the fan beam.

On the other hand, as shown in FIG. 7 (which displays one element of the collimating means intercepting one small arc of the fan beam and lying perpendicular to the plane thereof), a preferred third embodiment of collimator 23 avoids total attenuation of the scattered X-ray beam at any scattering angle without the requirement for rotational motion of the collimator. In this embodiment the collimator 23 may be employed with either the collimator sheets at constant angular spacings or at a range of angular spacings in the plane of FIG. 1, as given by equation (2). However, over a small arc of the fan beam, centered on the plane of FIG. 1, (typically having a maximum dimension at the object under inspection of approximately 1 cm), the sheets are rotated from perpendicular to the plane of FIG. 1 by an angle, typically in the range of 5 to 25 but more especially around 15 degrees, about an axis which is coincident with the radius of a circle centered at P and lying in the plane of FIG. 1. By this means the attenuation of the scattered X-ray beam is made small and closely equivalent at all scattering angles when the summed signal passing through the collimator from all of the target volume irradiated by the small arc of the fan beam concerned is accumulated.

Preferably the angular position of each sheet is such that when viewed from the front or rear face of the collimator, the nearest face of each sheet extends between the points at which the nearest face of adjacent sheets strike the limit of the small arc of the fan beam concerned in the plane of the front or rear face of the collimator as shown in FIG. 7. Shown generally at 28 is a supporting structure used to orientate and locate the collimator sheets.

Due to the divergence of the collimator sheets 23 in the direction away from the source towards the detector, the aforementioned angle of rotation of each sheet in a small arc of the fan beam centered on the plane of FIG. 1 about an axis from P in the plane of FIG. 1 advantageously varies with the distance from P along this axis, in other words the sheets are actually twisted along their length. Most preferably the angle of rotation at any given point on each sheet will be linearly proportional to the distance of that point from the scattering voxel centre.

Figure 5A:
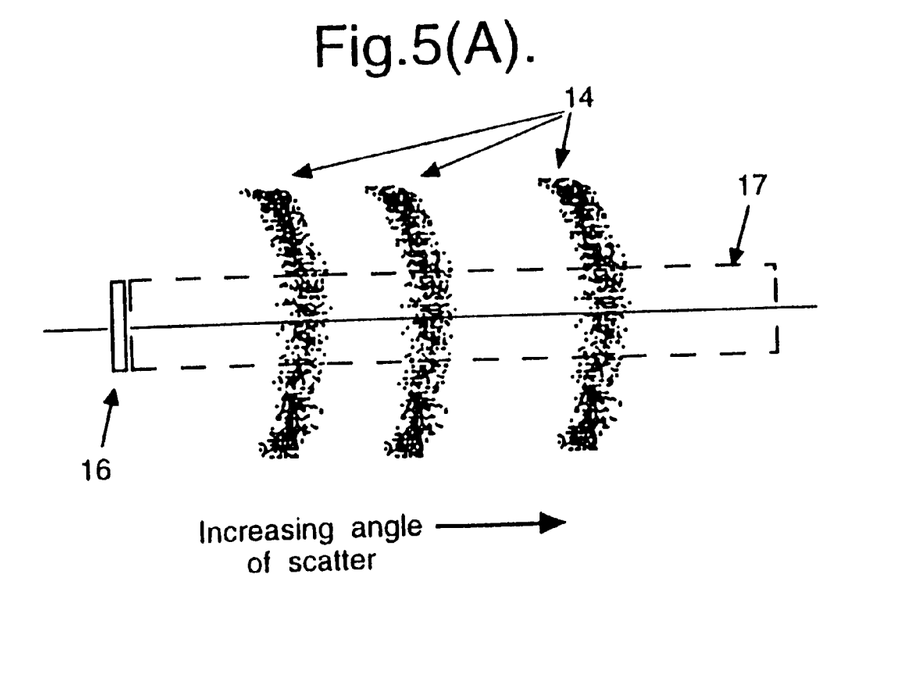
Figure 5B:
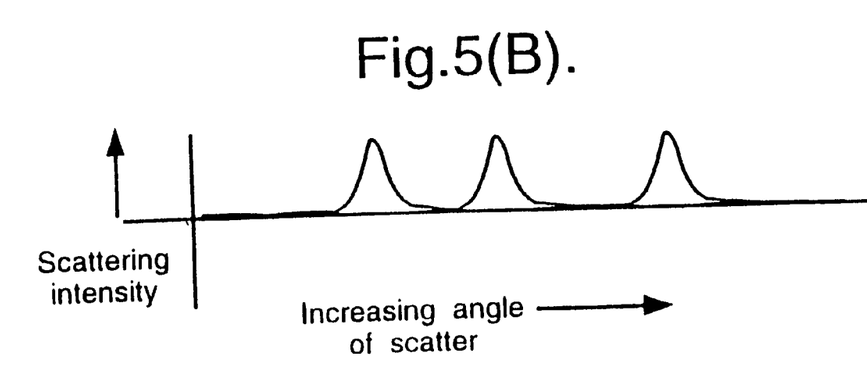

The scattering image produced by the differential image calculators 9a . . . n is illustrated in FIG. 5A where the scattering bands 14 correspond to part of the concentric rings of X-ray photons coherently scattered by the target voxel. The region of a detector 6a . . . n irradiated by unscattered X-rays is represented by 16 and the area used to generate the reduced information scattering profile of FIG. 5B is represented by the broken lines 17. As can be seen from FIG. 5B peaks in the intensity of scattered X-rays correspond to the scattering bands 14.

Figure 8:
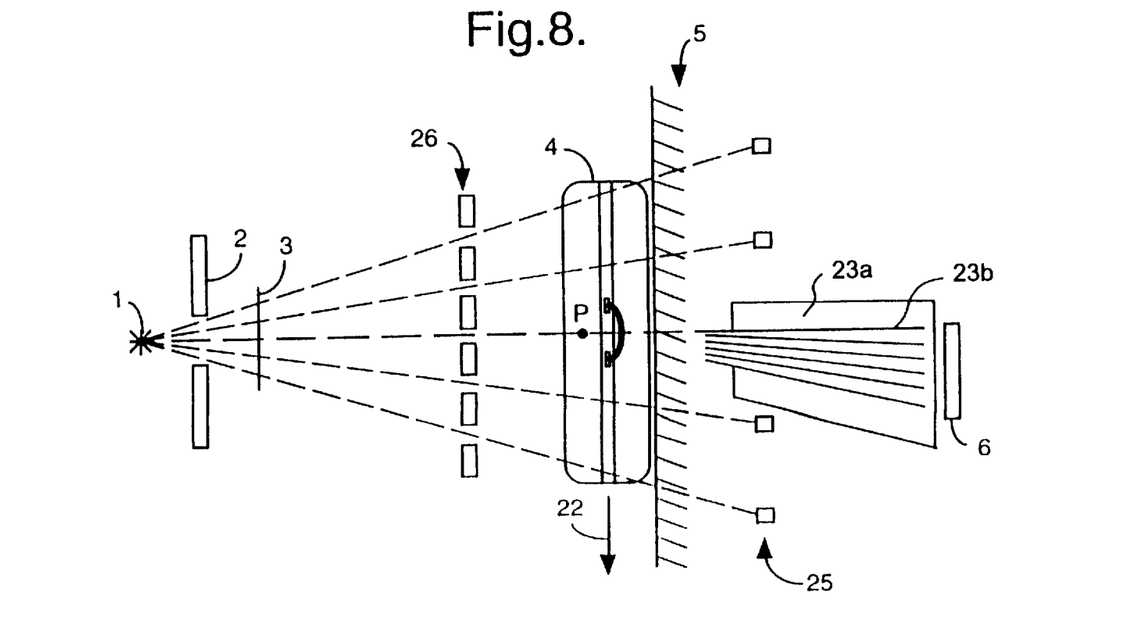
FIG. 8 illustrates a method of implementing low resolution tomographic attenuation correction.

FIG. 8 shows a further embodiment in which the apparatus previously described is supplemented with two or more linear array X-ray detectors 25 and an equivalent number of collimating slits 26. Each of the linear detector arrays 25 is used to measure the transmission of a narrow fan beam through the object under inspection along substantially different pathways at substantially different angles to the object. In a preferred embodiment each linear detector array is parallel to a chord between the extreme ends of the longest arc of the fan beam used to measure coherent X-ray scattering spectra and therefore extends perpendicularly to the plane of FIG. 8. Each linear detector array records a full linescan two dimensional transmission projection image of the complete object under test as the object passes on the conveyor through the associated fan beam. The linescan images from the plurality of these linear detector arrays can then be used to reconstruct a model of the three dimensional attenuation of the object under test using known tomographic methods such as outlined in U.S. Pat. No. 4,730,350. This information is preferably obtained using the thulium and erbium balanced filter technique described above and hence over a small range of X-ray photon energies substantially the same as that used to determine the coherent X-ray scattering spectra of the same object. The three dimensional attenuation model of the object can then be used to correct angle dispersive scattering spectra and remove attenuation effects from materials outside the scattering voxel in the unscattered primary beam and the arc of the scattered photon beam.

In practice only low spatial resolution tomographic images might be required for the purpose of attenuation correction of coherent X-ray scattering spectra and thus instrumentation which makes only relatively few X-ray transmission measurements over a small number of trajectories through the bag at various angles would be used. This would particularly be the case in a preferred embodiment where the motion of the suitcase on the conveyor during signal acquisition would increase the effective dimension of the scattering voxel and any item within the object under test along the axis of motion.

Figure 6:
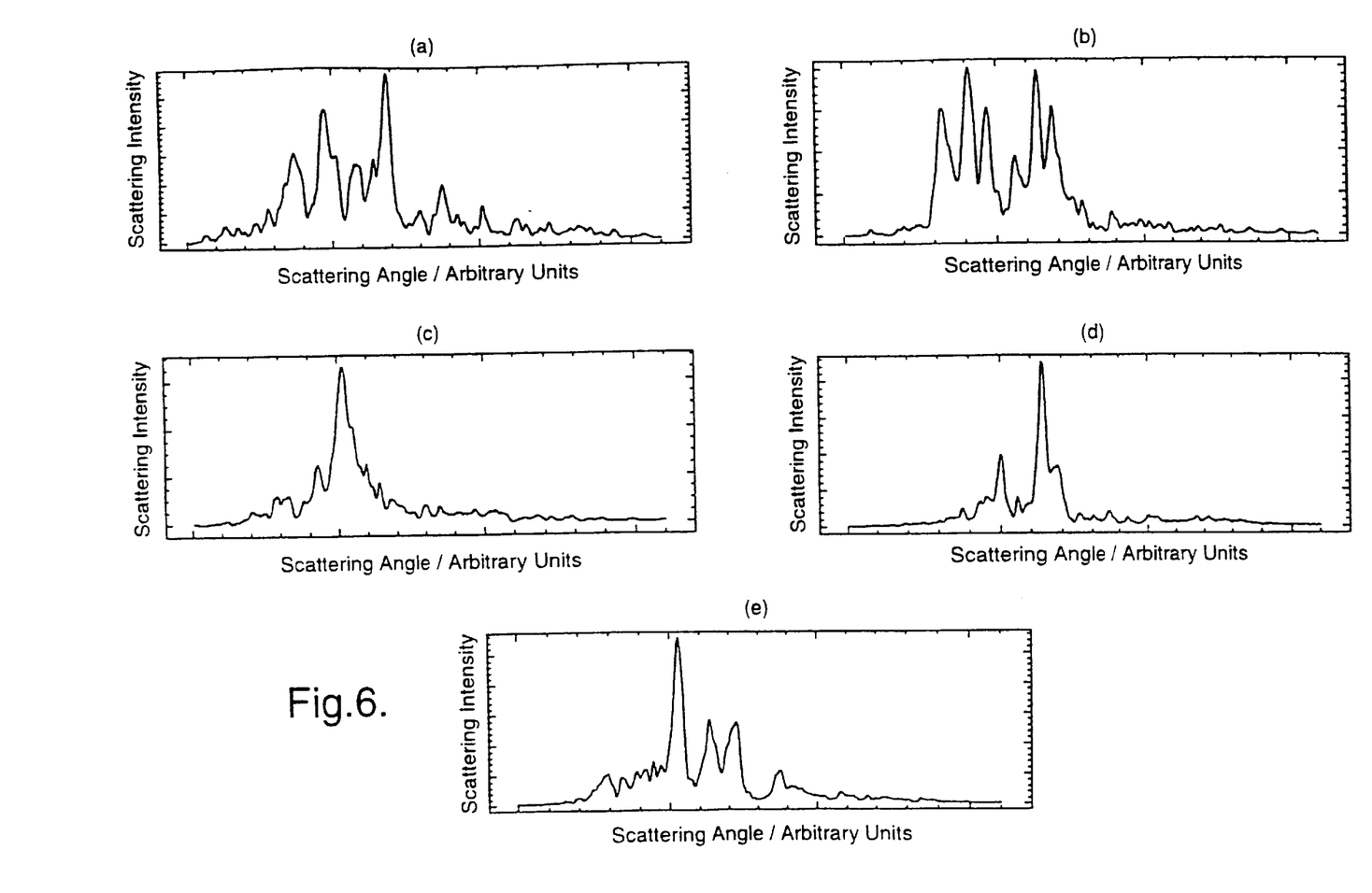
FIG. 6 shows representative scattering profiles obtained using different explosives.

FIG. 6 shows the scattering profiles obtained using the embodiment of FIGS. 1 and 2 from 13 mm thick samples of:

(a) HMX explosive;
(b) RDX-based plastic explosive;
(c) PETN-based sheet explosive;
(d) gunpowder
(e) ammonium nitrate/fuel mixture

What is claimed is:

1. An X-ray inspection system comprising:
   a collimated X-ray source disposed to produce a beam of X-rays in the form of a fan projected from the source towards an object,
   a focusing collimation means disposed to pass only X-rays scattered from a voxel element at a particular depth within the object,
   a detection means, responsive to X-rays from said collimation means, capable of discrimination of X-ray intensities with respect to position of incidence on the detection means and thereby arranged to produce an output signal representing X-ray intensity variation across an angular scattering range, and
   an analyzing means for processing the output signal to determine the presence of X-rays coherently scattered through at least one predetermined angles,
   wherein the focusing collimation means and X-ray fan beam are mutually arranged such that the collimation means is of constrained height in a parallel direction to a plane occupied by the fan beam and thus arranged so as to inhibit transmission through the collimation means of X-rays scattered from neighboring voxel elements onto which the X-ray beam is also incident.

2. An X-ray inspection system as claimed in claim 1 wherein the collimation means comprises a plurality of sheets of X-ray attenuating material, the sheets extending such that in any scattering plane each sheet describes part of a straight line passing through the centre of the voxel from which scatter may be detected.

3. An X-ray inspection system as claimed in claim 2 wherein the plurality of sheets are spaced apart from each other by the same small angle.

4. An X-ray inspection system as claimed in claim 2 wherein the angular separation between successive sheets is different, the separation being such that the sheets define a voxel which has a constant depth for each of the different angles through which X-rays may be coherently scattered.

5. An X-ray inspection system as claimed in claim 2 wherein each of the sheets lies wholly in a plane which is substantially perpendicular to the scattering plane which bisects the fan beam.

6. An X-ray inspection system as claimed in claim 2 wherein each of the sheets is arranged so as to lie along a surface which is not substantially perpendicular to the scattering plane which bisects the fan beam but which is rotated from this position through an angle which is not substantially greater than 25° about an axis which bisects the fan beam.

7. An X-ray inspection system as claimed in claim 6 wherein the angle of rotation is in the range of from 5 degrees to 25 degrees.

8. An X-ray inspection system as claimed in claim 7 wherein the angle of rotation is about 15 degrees.

9. An X-ray inspection system as claimed in claim 6 wherein the angle of rotation of a surface along which a sheet lies varies, along said axis of rotation, with distance from the scattering voxel centre.

10. An X-ray inspection system as claimed in claim 9 wherein the angle of rotation at any position on a surface upon which a sheet lies is linearly proportional to the distance of that position from the scattering voxel centre.

11. An X-ray inspection system as claimed in claim 2 wherein said sheets of the collimator means are rotatable about the centre of the scattering voxel in a plane substantially parallel to the scattering plane which bisects the fan beam, through an angle which is of the order of the angular spacing of the sheets.

12. An X-ray inspection method using the system in claim 11 wherein time taken for rotation of the collimation means through the angular spacing angle is not greater than the time taken for the detection means to generate a scattering profile.

13. An X-ray inspection system as claimed in claim 1 wherein the collimation means is moveable relative to the object to be inspected in the direction of the unscattered X-ray beam so as to vary the position of the voxel through the depth of the object.

14. An X-ray inspection system as claimed in claim 13 wherein the detection means is adapted to move with the collimation means.

15. An X-ray inspection system according to claim 1 wherein the system includes an array of focusing collimation means and a respective array of detection means, each member of the collimation means array being stacked in the direction of its constrained height so as to each admit X-rays scattering from respective limited arcs of the fan beam.

16. An X-ray inspection system as claimed in claim 1 wherein the X-ray source comprises a polychromatic x-ray generator and a co-operable balanced filter system.

17. An X-ray inspection system as claimed in claim 16 wherein the detection means comprises a detector adapted to be sensitive to substantially only that X-ray energy within the band-pass region of the balanced filter system.

18. An X-ray inspection system comprising:
   a collimated X-ray source disposed to produce a beam of X-rays in the form of a fan projected from the source toward an object,
   a detector determining the intensity of coherently scattered X-rays at different scattering angles and producing an output signal dependent on the intensity of X-rays scattered through each of those angles,
   a collimator, disposed between the detector and the object, passing to said detector only X-rays that have been coherently scattered from a limited voxel depth through various angles and that lie in planes which are substantially parallel to a scattering plane which passes through the source and the centre of the voxel from which scattering occurred and which is perpendicular to the plane of the fan beam, and
   an analyser, responsive to the detector, processing the output signal to determine the presence of X-rays coherently scattered through at least one predetermined angles.

19. An X-ray inspection system in accordance with claim 18 wherein said collimator and detector are movable relative to said object in a direction having a component in the direction of said object.

20. An X-ray inspection system comprising:
   a collimated X-ray source disposed to produce a beam of X-rays in the form of a fan projected from the source toward an object,
   a detection means capable of determining the intensity of coherently scattered X-rays at different scattering angles and producing an output signal dependent on the intensity of X-rays scattered through each of those angles,
   a collimation means, disposed between the detection means and the object, for passing to said detection means only X-rays that have been coherently scattered from a limited voxel depth through various angles and that lie in planes which are substantially parallel to a scattering plane which passes through the source and the centre of the voxel from which scattering occurred and which is perpendicular to the plane of the fan beam, and
   an analysing means, responsive to the detection means, for processing the output signal to determine the presence of X-rays coherently scattered through at least one predetermined angles.

* * * * *